(12) United States Patent
Hogstrom et al.

(10) Patent No.: US 10,751,549 B2
(45) Date of Patent: Aug. 25, 2020

(54) PASSIVE RADIOTHERAPY INTENSITY MODULATOR FOR ELECTRONS

(71) Applicants: Kenneth Hogstrom, Baton Rouge, LA (US); Robert Carver, Baton Rouge, LA (US)

(72) Inventors: Kenneth Hogstrom, Baton Rouge, LA (US); Robert Carver, Baton Rouge, LA (US)

(*) Notice: Subject to any disclaimer, the term of this patent is extended or adjusted under 35 U.S.C. 154(b) by 0 days.

(21) Appl. No.: 16/039,251

(22) Filed: Jul. 18, 2018

(65) Prior Publication Data

US 2020/0023200 A1    Jan. 23, 2020

(51) Int. Cl.
*A61N 5/10* (2006.01)

(52) U.S. Cl.
CPC ........... *A61N 5/1047* (2013.01); *A61N 5/103* (2013.01); *A61N 5/1065* (2013.01); *A61N 5/1077* (2013.01); *A61N 2005/1089* (2013.01)

(58) Field of Classification Search
CPC ............. H01J 37/3177; H01J 2229/507; H01J 2229/075; H01J 2229/0755; H01J 2229/0761; H01J 2229/0727; H01J 2229/0733; A61N 5/1042; A61N 5/1077; A61N 5/1078; A61N 2005/1089; A61N 2005/1095; G21K 1/10; H05H 7/00; H05H 7/12; H05H 2007/004; H05H 2007/125
See application file for complete search history.

(56) References Cited

U.S. PATENT DOCUMENTS

| | | | | |
|---|---|---|---|---|
| 4,419,585 A | * | 12/1983 | Strauss | G21K 1/025 250/363.1 |
| 4,672,648 A | * | 6/1987 | Mattson | G21K 1/025 378/149 |
| 5,479,469 A | * | 12/1995 | Fraser | G21K 1/025 250/505.1 |

(Continued)

*Primary Examiner* — Nicole M Ippolito
*Assistant Examiner* — Sean M Luck (57) ABSTRACT

Typically, electron beam radiation therapy aims at delivering a uniform dose to a target volume containing cancer cells. Electron sources typically impinge a spatially uniform flux across the beam onto the patient; however, irregular patient and bolus surfaces, the latter encountered in bolus electron conformal therapy (ECT), scatter electrons unevenly creating non-homogeneous dose distributions in the target. However, spatially-modulated beam intensities can restore target dose homogeneity, as well as enable utilization of other advanced ECT methods. Unfortunately, present methods, which have attempted to spatially-modulate beam intensities, have been either impractical or ineffective. Here, a novel, passive method has been developed to spatially-modulate electron beam intensities by taking advantage of multiple Coulomb scattering. The method utilizes Island Blocks or Island Apertures, strategically located in 'transparent' or 'opaque' substrates, respectively, which are placed in the beam's path. This method spatially-modulates electron flux across the beam with insignificant loss of electron beam energy. Thus, delivering a uniform, highly conformal dose distribution to the target volume is possible. Further, the method is inexpensive and can be easily incorporated into existing electron therapy machines.

23 Claims, 6 Drawing Sheets

(56) References Cited

U.S. PATENT DOCUMENTS

| | | | | |
|---|---|---|---|---|
| 5,528,659 A * | 6/1996 | Stein | | G21K 1/025 |
| | | | | 378/149 |
| 5,621,270 A * | 4/1997 | Allen | | B01D 53/323 |
| | | | | 250/492.3 |
| 5,924,277 A * | 7/1999 | Beattie | | F03H 1/0043 |
| | | | | 313/360.1 |
| 6,127,688 A * | 10/2000 | Wu | | G21K 1/025 |
| | | | | 250/492.3 |
| 6,353,227 B1 * | 3/2002 | Boxen | | G21K 1/025 |
| | | | | 250/363.06 |
| 6,408,054 B1 * | 6/2002 | Rahn | | G21K 1/10 |
| | | | | 378/149 |
| 6,864,485 B2 * | 3/2005 | Kahn | | H01J 27/024 |
| | | | | 250/396 ML |
| 6,870,174 B2 * | 3/2005 | Yamaguchi | | H01J 33/04 |
| | | | | 250/492.3 |
| 7,345,290 B2 * | 3/2008 | Katsap | | H01J 37/065 |
| | | | | 250/396 R |
| 9,159,522 B2 * | 10/2015 | Poppi | | H01J 5/18 |
| 9,299,469 B2 * | 3/2016 | Larson | | G21K 1/00 |
| 2002/0130606 A1 * | 9/2002 | Suzuki | | H01J 29/07 |
| | | | | 313/407 |
| 2003/0198319 A1 * | 10/2003 | Toth | | A61B 6/032 |
| | | | | 378/159 |
| 2006/0253510 A1 * | 11/2006 | Kameyama | | G06F 17/50 |
| | | | | 708/200 |
| 2007/0114432 A1 * | 5/2007 | Kristiansson | | A61L 2/087 |
| | | | | 250/397 |
| 2008/0037709 A1 * | 2/2008 | Yatsenko | | G21K 1/10 |
| | | | | 378/145 |
| 2008/0049897 A1 * | 2/2008 | Molloy | | A61N 5/1042 |
| | | | | 378/65 |
| 2010/0061511 A1 * | 3/2010 | Heid | | G21K 1/04 |
| | | | | 378/65 |
| 2011/0012495 A1 * | 1/2011 | Walther | | G21K 5/00 |
| | | | | 313/46 |
| 2011/0210256 A1 * | 9/2011 | Mattson | | G01T 1/00 |
| | | | | 250/363.01 |
| 2012/0222815 A1 * | 9/2012 | Sabri | | C23C 16/45565 |
| | | | | 156/345.34 |
| 2013/0000253 A1 * | 1/2013 | berg | | H01J 33/04 |
| | | | | 53/425 |
| 2013/0094993 A1 * | 4/2013 | Linne | | H01J 33/04 |
| | | | | 422/22 |
| 2013/0140474 A1 * | 6/2013 | Cloetta | | G21K 5/02 |
| | | | | 250/505.1 |
| 2014/0112431 A1 * | 4/2014 | Mattson | | G21K 1/10 |
| | | | | 378/16 |
| 2014/0141619 A1 * | 5/2014 | Sawada | | H01J 37/32091 |
| | | | | 438/711 |
| 2014/0209820 A1 * | 7/2014 | Barry | | H01J 33/04 |
| | | | | 250/505.1 |
| 2014/0294154 A1 * | 10/2014 | Slatkin | | A61N 5/1042 |
| | | | | 378/65 |
| 2015/0028220 A1 * | 1/2015 | Poppi | | C23C 28/322 |
| | | | | 250/423 R |
| 2015/0053640 A1 * | 2/2015 | Kostamo | | B82Y 30/00 |
| | | | | 216/24 |
| 2015/0214013 A1 * | 7/2015 | Glukhoy | | H01J 37/32449 |
| | | | | 29/527.1 |
| 2015/0302946 A1 * | 10/2015 | Ofer | | A61B 6/06 |
| | | | | 378/160 |
| 2015/0357150 A1 * | 12/2015 | Kostamo | | H01J 5/18 |
| | | | | 378/161 |
| 2016/0181056 A1 * | 6/2016 | Alexy | | H01J 37/09 |
| | | | | 250/396 R |
| 2016/0361449 A1 * | 12/2016 | Omrane | | A61L 2/087 |
| 2017/0256378 A1 * | 9/2017 | Arai | | G01T 1/18 |
| 2017/0368373 A1 * | 12/2017 | Sahadevan | | A61N 5/1084 |

* cited by examiner

PASSIVE RADIOTHERAPY INTENSITY MODULATOR FOR ELECTRONS

CROSS REFERENCE

The present application claims benefit of U.S. Provisional Patent Application No. 62/533,923, filed 18 Jul. 2017, which is hereby incorporated by reference herein in its entirety, including but not limited to those portions that specifically appear herein.

FIELD OF THE INVENTION

Electron beam therapy ("EBT") is one form of radiation treatment of patients, particularly those patients with certain forms of cancer where the target cells are found in tissues within 6 cm of the surface.

Typically, the energy of an electron beam used in EBT is between about 6 and 20 million electron volt ("MeV").

Other radiation sources, including X-rays (photon beams) and charged heavy particle beams (typically proton beams), also are used to treat cancer.

When treating a patient, a distribution of dose, typically uniform, is prescribed to a specified volume of tissue, often called the planning target volume (PTV), which typically is the volume containing the targeted cancer cells plus some margin.

As a radiation beam penetrates the patient's body (or other target), the radiation beam deposits energy. The deposition of energy per unit mass is defined as radiation dose.

The physical mechanisms by which these beams deposit dose depend on the modality of the radiation, i.e. electrons, protons, or photons. Further, scattering of radiation beams affects the deposition of dose. As an X-ray or photon beam penetrates a body, its dose deposition decreases approximately exponentially. A proton beam penetrates a fixed depth (defined as the range) in the body, depositing a sharp peak of dose just before stopping, that depth depending on the beam energy. Hence, a proton beam requires energy modulation in order to spread its peak dose over the PTV size in the direction of the beam. An electron beam also penetrates a fixed depth in the body, depositing dose approximately uniformly for approximately 67% of its range, then decreasing continuously over the next few cm.

It is desirable to control the spatial distribution (modulation) of the incident intensity or flux of a beam. As used herein, the terms intensity and flux are used to mean the number of charged particles or photons per unit area at a position in a radiation beam, which impacts a target.

When treating a patient, it is normally desirable for there to be a near uniform dose within the PTV, while at the same time minimizing dose to healthy tissues. Treatment of deep seated PTVs requires either high energy X-ray or proton beams, each having multiple beams incident from different directions. Often the best treatments require these beams to be intensity modulated, called intensity modulated X-ray therapy (IMXT) or intensity-modulated proton therapy (IMPT). Hence, many X-ray treatments require beams from multiple directions, each beam having intensity modulation. Similarly, many proton treatments require beams from multiple directions, each beam having energy (or range) and intensity modulation.

Superficial PTVs can be treated with electrons, and often the best treatment is delivered by electron conformal therapy (ECT), requiring energy and intensity modulation. Bolus electron conformal therapy (BECT) normally uses a single beam of sufficient energy to reach the deepest part of the PTV; then energy (range) in the patient is modulated by a variable thickness of approximately unit density material (e.g. wax) called bolus. However, electrons scattering from the non-uniform surface of the bolus or of the patient's body cause the dose in the PTV to be non-uniform, which can be removed by intensity modulation (IM) referred to as IM-BECT.

A second ECT method, called Segmented Field ECT, utilizes multiple, abutted fields from the same direction, but of differing energy. Being of different energies, two abutting fields have differing penumbral widths, resulting in volumes of increased and decreased dose (referred to as hot spots and cold spots), which can be removed by using intensity modulation to broaden the sharper of the two penumbras to match the other. A third method, coined modulated electron radiation therapy (MERT) utilizes modulated beams of differing beam energy and directions. Hence, all three methods of ECT require intensity modulation.

X-rays and protons, at the energies used for treating cancer patients, exhibit little scattering in the air between the beam source and the patient. Thus, intensity modulation for X-ray beams has been done with little difficulty using dynamic multileaf collimators (MLCs) located far (60-70 cm) from the patient. MLCs form multiple beams, each of differing shapes and intensities, so when summed form any specified intensity distribution. However, electron beams show significant scattering in the intervening air, so that X-ray MLCs cannot be used for electron intensity modulation. The air scatter prohibits the required intensity modulation at standard treatment distance, and although reduced treatment distances partially resolve that problem (issues with scattering from the side of X-ray leaves remain), they place the treatment table and patient at unsafe, impractical positions. Hence, X-ray MLCs have not emerged as a solution for electron intensity modulation.

Passive methods for achieving X-ray intensity modulation utilize metallic blocks of variable thickness, which control intensity versus position by controlling X-ray attenuation versus position. These devices, called X-ray compensators, are highly effective, but cannot be used for electrons because electrons are not attenuated.

Protons, because of their large mass, do not show significant scatter in air; hence, proton beam intensity modulation has been achieved by magnetic beam scanning, which varies the proton intensity as orthogonal bending magnets scan the beam over a PTV. Beam scanning is highly effective for proton beams, but cannot be used for electrons because of their significant amount of scatter by intervening air and the end window of the accelerator.

The invention disclosed herein describes a novel method for passive radiotherapy intensity modulation for electrons (referred to sometimes as 'PRIME').

BACKGROUND AND DESCRIPTION OF PRIOR ART

Three types of electron conformal therapy ("ECT") either require or could benefit from intensity modulated (IM) electron beams: segmented-field ECT, bolus ECT, and modulated electron radiation therapy ("MERT"); however, no reliable method for IM of ECT is available.

Intensity modulation of an X-ray beam has been accomplished using multileaf collimators ("MLCs"), which are collimators with an assemblage of "leafs" which selectively block sections of an X-ray beam. Attempts that have been made to deliver electron intensity modulation using photon MLCs have proven unsuccessful. When X-ray MLCs are used with electron beams, scattering in the large air gap between the MLCs and the PTV nullifies any useful modulation of the electron beam. Thus, photon MLCs have been ineffective in IM for ECT.

Electron multileaf collimators ("eMLC") have been made and are commercially available, but because these devices are heavy, cumbersome, not permanently attached to the electron accelerator, and expensive, few if any eMLCs are used. Further, eMLCs must be placed very close to the patient, for example within 10-15 cm, which makes it even more difficult to use an eMLC. In comparison, photon MLCs typically are placed about 60-70 cm from the patient and are attached to the electron accelerator.

Proton beam IM, best achieved by modulating the beam as it is magnetically scanned across the PTV, is possible due to proton multiple Coulomb scattering (MCS) in air being of such small magnitude (few mm). Such is not the case for electrons. Even replacing the intervening air with a gas such as helium, which causes relatively low MCS, is insufficient due to MCS from the accelerator end window and ion chamber. Furthermore, scanning electron beams have remained off the market since the 1990s as a result of deadly accidents that occurred with scanned electron beam machines. These approaches are impractical for routine treating of patients, and thus to date, these approaches remain commercially unavailable.

Although not actually IM, when EBT is used to treat an eye retina, a single island is placed over the patient's eye. Such an island blocks the electron beam from directly impinging on the underlying lens, which is at a shallow depth (0.3 cm), thereby reducing the possibility of blindness or cataracts formation. However, electron MCS allows the underlying retina, which is at a deeper depth (3.0 cm), to receive about 70% of the prescribed dose.

Also not actually IM, on some occasions, EBT utilizes two or more electron beams having different energies (also known as Segmented Field ECT). However, due to differing beam energies or beam misalignment, unwanted hot spots and/or cold spots can result in the treatment volume. To reduce these unwanted results, saw-toothed collimator edges have been used to match the electron penumbra (e.g. 80%-20% dose edge) for abutting beams of differing energies.

The invention disclosed herein is a novel method for passive electron intensity modulation that comprises inserting a plurality of Island Blocks (sometimes referred to as "Islands") and/or Island Apertures (sometimes referred to as "Apertures") in the path of an electron beam. This method provides control of electron beam intensity modulation within the treatment field and in the penumbra. The pattern of Island Blocks and/or Island Apertures may be optimized for any particular EBT treatment. This method is low-cost and can be easily incorporated into most existing clinical settings.

SUMMARY OF THE INVENTION

A novel method for Passive Radiotherapy Intensity Modulation for Electrons ("PRIME") is disclosed herein. This novel method utilizes a simple insert placed in or near the aperture of an electron beam collimator, which generates an arbitrary intensity pattern as a result of electron beam scattering by air above the collimator and subsequent drifting from the collimator to the PTV. This method is inexpensive and can be used with existing electron beam sources with minimal changes.

PRIME delivers a therapeutic electron beam intensity, in a plane perpendicular to the central electron beam axis, which may be modulated in a controlled manner across the treatment field.

PRIME comprises a method of allowing an electron beam, generated in a manner well known to those in the field, to pass through an intensity modulator comprising a collection of small area Island Blocks placed inside or adjacent to a collimating insert and/or a collection of small Island Apertures placed throughout the collimating insert. The intensity modulator impinges the specified intensity modulated electron beam on the target. Island Blocks, as used herein, are defined as an array of solid, electron blocking posts or rods implanted in an electron transparent substrate (e.g. thin, low-density, machineable foam slabs). Island Apertures, as used herein, are holes or electron transparent pathways arrayed on an electron collimating substrate (e.g. lead, Cerrobend, or copper). A collimating insert, as used herein, is a device placed in the path of an electron beam for the purpose of shaping the cross section of the beam to that best suited to irradiate the patient PTV.

The Island Blocks may vary in height, shape, cross sectional area, and spacing between Islands. The Island Apertures may vary in height, shape, diameter, and spacing between Apertures. The Island Blocks must be constructed of medically non-hazardous electron-blocking material, such as tungsten, titanium, lead, lead alloy, copper, steel, nickel, or other suitable heavy metals or their alloys. The Island Blocks are placed into a thin, low-density, substrate (e.g. low-density machineable foam) that is placed inside or near the electron field-defining metal (e.g. Cerrobend or copper) collimating insert that defines the beam shape. The Island Apertures are holes in the collimating insert, which vary in shape, diameter, and spacing between Apertures. Under normal circumstances, the central axes of the Island Blocks and Island Apertures will closely coincide with rays diverging from the virtual electron source.

DETAILED DESCRIPTION OF THE INVENTION

The method comprises selecting the areas of the Island Blocks or Island Apertures, selecting the shape of the Island Blocks or Island Apertures, selecting the separation between Island Blocks or Island Apertures, precisely locating the Island Blocks in an electron-transparent substrate, or for Island Apertures, locating the hole or aperture precisely through an electron-blocking substrate, and placing the Island Blocks or Island Apertures in the path of an electron beam. When the electron beam passes through the Island Blocks and/or the Island Apertures, a desired intensity-modulated, non-homogenous flux of electrons is delivered to a target.

Figure 1:
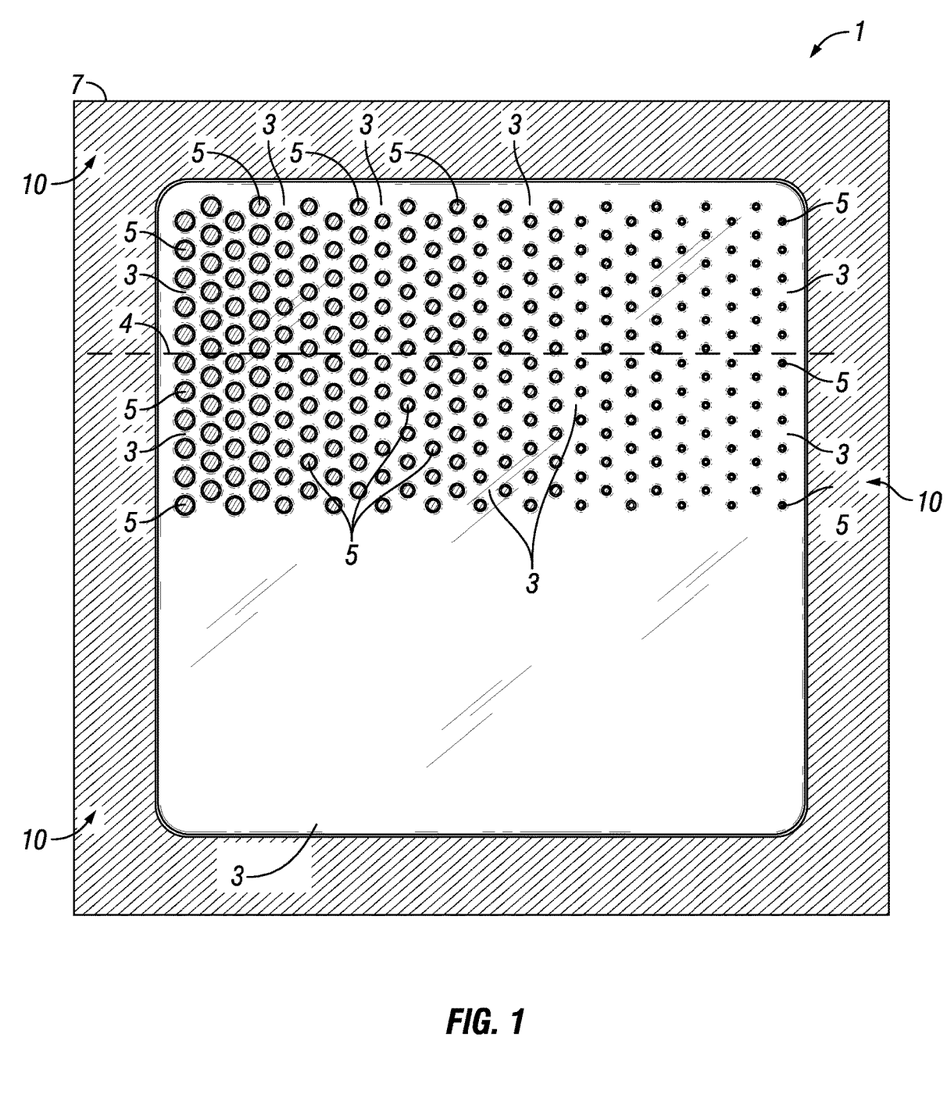
FIG. 1 displays a beam's eye view (looking down the central axis of a beam from the virtual radiation source) of a prototype electron beam intensity modulator containing only Island Blocks.

FIG. 1 displays a prototype electron beam intensity modulator [1] using Island Blocks, which is located inside the aperture of the collimating insert [10]. The figure shows an electron transparent substrate [3] into which a plurality of Islands [5] are imbedded. Typically, the Islands [5] are sized and spaced in a manner to optimize the spatial distribution of electron beam intensity at a target, for example, a patient. This prototype is a test pattern in which Island Blocks are equally spaced and have systematic changes in diameter.

Figure 2:
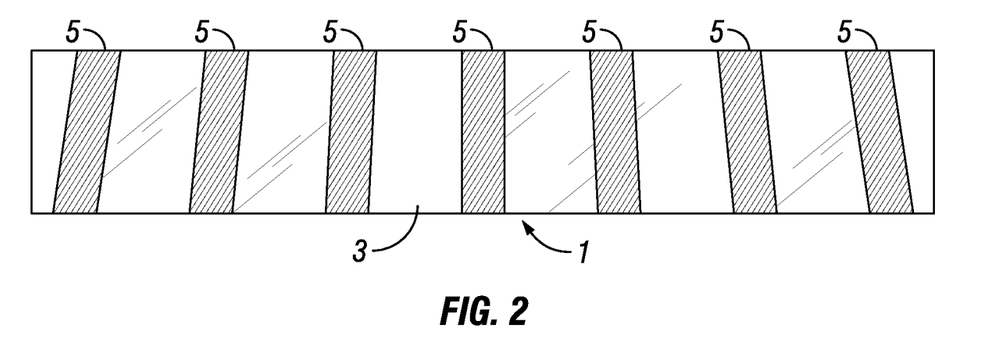
FIG. 2 displays an Island Block model showing a side view of the Islands in an electron-transparent substrate.

FIG. 2 provides a side view of a portion of a cut through an electron beam intensity modulator [1] using Island Blocks, showing the electron transparent substrate [3] and the Island Blocks [5] opaque to the electrons (stops and absorbs electrons).

Figure 3:
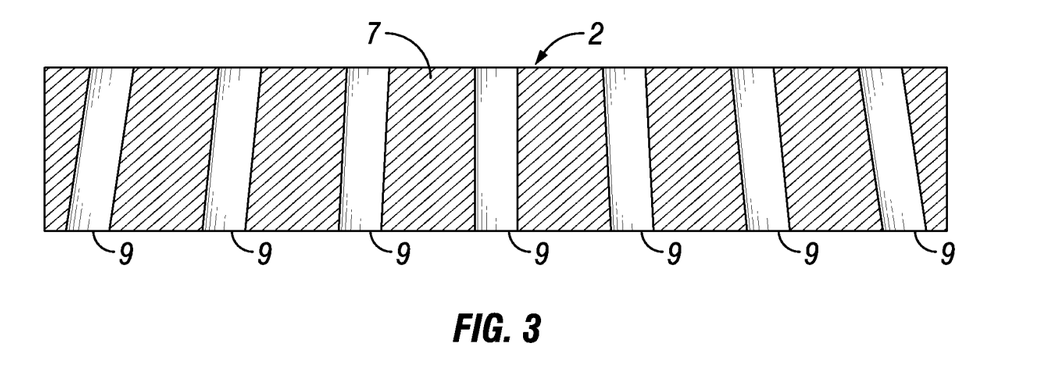
FIG. 3 displays an Island Aperture model showing a side view of the Apertures in an electron-blocking substrate.

FIG. 3 provides a side view of a portion of a cut through an electron beam intensity modulator [2] using Island Apertures, where the substrate [7] is opaque to electrons and the Apertures [9] allow passage of the electrons.

Figure 4:
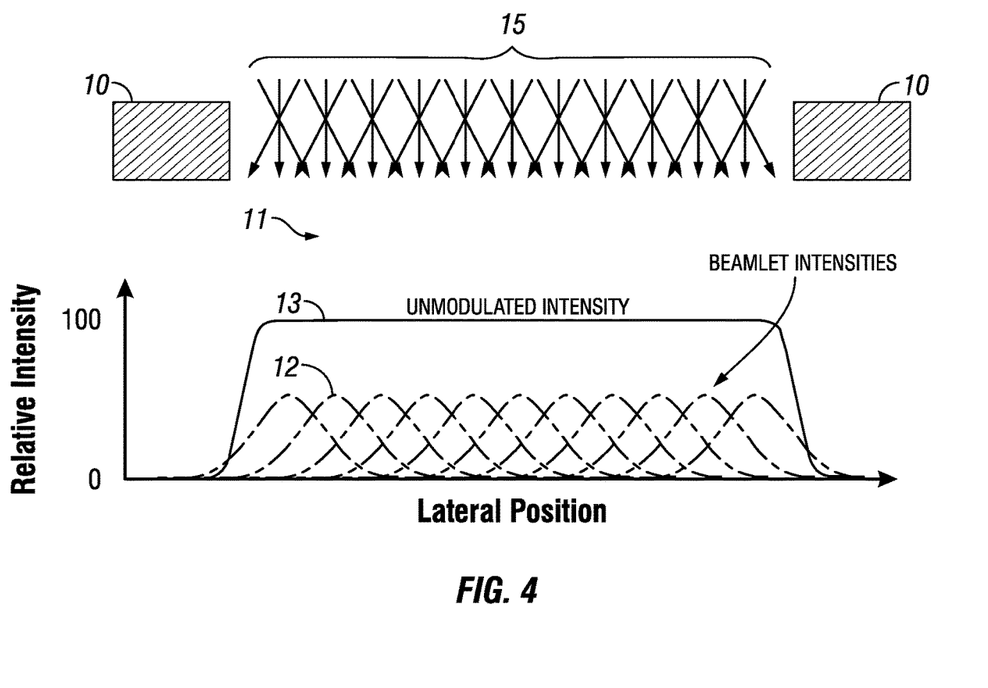
FIG. 4 displays a depiction of the electron intensity when an electron beam passes through air without an electron beam intensity modulator.

Whereas in general EBT is hindered by electron multiple Coulomb scattering (MCS), this method takes advantage of MCS by air, as an electron beam travels from its source to the target. As an electron beam encounters the array of Islands Blocks, some electrons pass through the substrate and some electrons are blocked (stopped and absorbed). As shown in FIG. 4, electrons at each point in the beam [15], having been scattered by air upstream of the electron collimator [10], spread as they drift through air [11] from the electron collimator [10] to the target plane. There the individual electron beamlet distributions [12] recombine, producing a relatively uniform manner [13] at a predictable depth.

Figure 5:
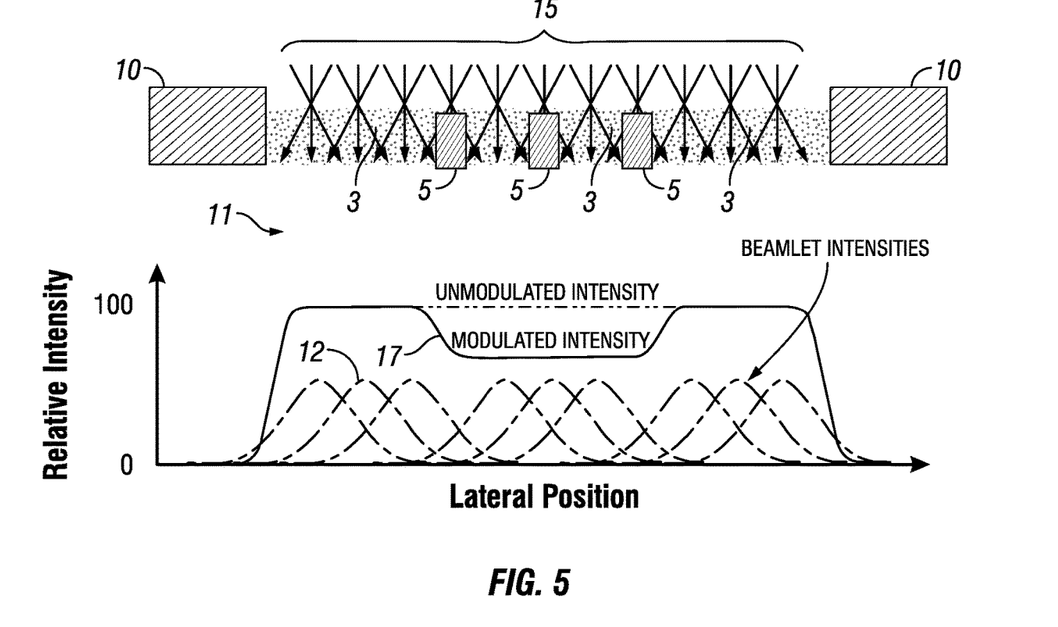
FIG. 5 displays a depiction of the electron intensity when an electron beam passes through an electron beam intensity modulator containing Island Blocks.

FIG. 5 illustrates the effect of placing the Island Blocks [5] in the path of an impinging electron beam [15]. Electrons at each point in the beam still spread as they drift through air [11] due to their being scattered by air upstream of the electron collimator [10], but some of the beam [15] is stopped by the Island Blocks [5]. Thus, when the electron beam recombines further downstream at the target, the resulting intensity [17] is non-uniform (modulated). Electrons that are not blocked still scatter and recombine at a predictable distance below the Island Blocks [5] in a predictable manner. The same mechanism applies for Island Apertures [9], except more of the electron beam is blocked and intensities will be lower.

Figure 6:
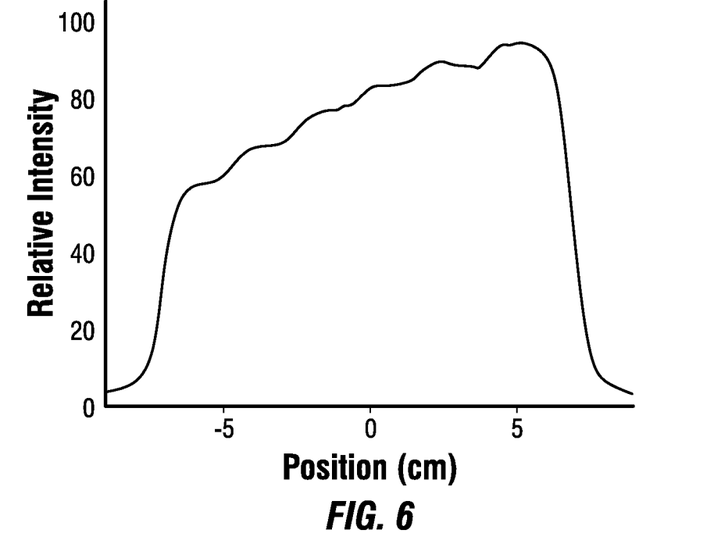
FIG. 6 displays a relative intensity profile 2 cm deep in water under a line through the middle of the set of Island Blocks in the upper half of the collimating insert (larger Blocks on left to smaller Blocks on right) for the prototype intensity modulator shown in FIG. 1.

Using this novel method, some electrons are blocked and thus never reach a target. Therefore, a distinct pattern of electron flux reaches the target. FIG. 6 displays an electron intensity profile of a 16 MeV electron beam at a depth of 2 cm in water (surface 5 cm downstream of intensity modulator) along a line passing through the center line [4] in FIG. 1 of a prototype passive radiotherapy intensity modulator for electrons (PRIME), where the relative intensity of the intensity modulated electron beam versus position is plotted at the target. The intensity of the resulting electron beam is selectively reduced or modulated at selected locations as the beam reaches a target. The distance below the PRIME containing Island Blocks [5] (or Island Apertures [9]) at which the scattered electron beamlets recombine, and the desired intensity is achieved, may be controlled by the size (area) and separation of the Islands [5] (or Apertures [9]).

Figure 7:
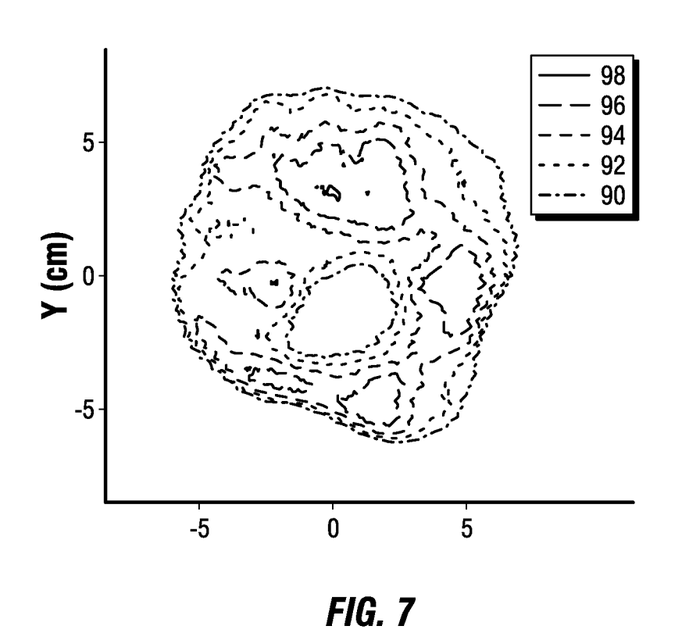
FIG. 7 displays the contour map of isointensity lines created by an electron beam after passing through the patient passive intensity modulator shown in FIG. 8 and designed using the method disclosed herein.

As an electron beam encounters a pattern of Island Blocks (or Island Apertures), modulation of the intensity of the electron beam occurs, thereby causing a non-uniform, predetermined intensity distribution to impinge the target tissue, which results in a nearly uniform dose to the patient PTV. FIG. 7 illustrates the dose modulation for a patient using the electron beam modulator displayed in FIG. 8. FIG. 7 is an isocontour map of a modulated intensity impinging on a patient. The topographical lines, 90, 92, 94, 96, and 98, represent the percentage of the full dose reaching that area in the absence of the intensity modulator.

Island Apertures [9] may be used instead of Island Blocks [5] when it is desirable for a higher fraction ($\geq 50\%$) of the electron beam to be blocked. Island Apertures [9] may be thought of as the inverse of Island Blocks [5]. FIG. 5 illustrates Island Blocks [5] stopping electrons, with the low-density substrate [3] allowing electrons to pass through. Inversely, FIG. 3 illustrates electrons passing through Island Apertures [9], with the collimating substrate [7] stopping the electrons.

The Island Blocks [5] comprise columns with essentially flat tops with shapes selected from circles, rectangles, squares, hexagons, or other polygons. The surface area of the sides of the columns should be minimized as compared to the surface area of the tops of the columns to minimize the fraction of electrons scattering into or from the column walls; hence, the most preferable cross sectional shape of the columns is circular. The columns may be parallel to the central axis of the beam (perpendicular to the substrate) or at other angles, most preferably at an angle aligned with the divergence of the beam (projected from the virtual source of the electron beam), again the latter to minimize the fraction of electrons scattering into or from the column walls.

The height or thickness of the Island Blocks (columns) [5] must be sufficient to completely block (stop) an electron beam at the energies typically used in EBT. The actual thickness depends on the material used for construction. For example, Island Blocks constructed of tungsten must be at least 0.6 cm thick for beams up to 20 MeV.

The diameters of cylindrical Island Blocks [5] are typically between about 0.1 cm and 1.0 cm, which for non-circular cross sections correspond to areas between about 0.008 $cm^2$ and 0.8 $cm^2$.

The substrate [3] into which the Islands [5] were imbedded comprises a low density material, such as a low density polymer.

For Island Apertures [9], the size of the Apertures [9], the thickness of the substrate [7] and the distance between Apertures [9] defines the modulated flux in the same manner as described for Island Blocks [5].

It is important to note that the novel method, PRIME, described herein, spatially modulates the intensity of an electron beam with insignificant change to the beam's mean energy or energy distribution.

For hexagonal packing of cylindrical blocks, the range of Island Block [5] diameters and separation parameters ("d, r") may be varied to determine the pattern of Intensity Reduction Factors ("IRF"), where $$IRF(d, r) = \left[1 - \left(\frac{\pi}{2\sqrt{3}}\right)\left(\frac{d}{r}\right)^2\right], \quad (1)$$

where d is the diameter of the cross section of the Island Blocks [5] and r is the distance between Island Blocks [5]. For non-circular cross sections, 2A $$IRF(d, r) = \left[1 - \left(\frac{2A}{\sqrt{3}\, r^2}\right)\right], \quad (2)$$

where A is the cross sectional area of the Island Blocks.

Circular Island Blocks packed in a hexagonal grid, for example, may be used for intensity modulated ECT, for which IRFs in the range of 0.70 to 1.00 are expected.

The resulting intensity of an electron beam is defined as follows:

$$I_{desired} = I_o * IRF, \quad (3)$$

where $I_o$ is the initial, unmodulated intensity of the electron beam.

Equation 4, which is a rearrangement of equation 1, may be used to determine the preferred diameter of cylindrical Island Blocks [5] at each point within a hexagonal grid, as shown below, $$d(r, IRF) = r\left[\frac{2\sqrt{3}}{\pi}(1 - IRF)\right]^{\frac{1}{2}}. \quad (4)$$

Each Island Block [5] may impact multiple locally desired intensities. Thus, the exact diameter and location of the Island Blocks [5] may be optimized to obtain the desired intensity distribution incident on the target.

Whereas Island Blocks [5] are likely more effective for $0.50 \leq IRF \leq 0.99$, Island Apertures are likely more effective for $0.01 \leq IRF \leq 0.50$. This minimizes the undesirable effect of electrons scattering into or out of the sides of the Island Blocks and Island Apertures.

For hexagonal packing of cylindrical Apertures, the range of Island Aperture [9] diameters and separation parameters ("d, r") may be varied to determine the pattern of Intensity Reduction Factors ("IRF"), where $$IRF(d, r) = \left(\frac{\pi}{2\sqrt{3}}\right)\left(\frac{d}{r}\right)^2, \quad (5)$$

where d is the diameter of the cross section of the Island Aperture [9] and r is the distance between Island Apertures [9]. For non-circular cross sections, $$IRF(A, r) = \frac{2A}{\sqrt{3}\, r^2}, \quad (6)$$

where A is the cross sectional area of the Island Apertures [9].

Circular Island Apertures [9] packed in a hexagonal grid, for example, may be useful for modulated electron radiation therapy (MERT), for which IRFs in the range of 0.01 to 1.00 are expected.

The resulting intensity of an electron beam is defined as follows:

$$I_{desired} = I_o * IRF, \quad (7)$$

where $I_o$ is the initial, unmodulated intensity of the electron beam.

Equation 8, which is a rearrangement of equation 5, may be used to determine the preferred diameter of cylindrical Island Apertures [9] at each point within a hexagonal grid, as shown below, $$d(r, IRF) = r\left[\frac{2\sqrt{3}}{\pi} IRF\right]^{\frac{1}{2}}. \quad (8)$$

Each Island Aperture [9] may impact multiple locally desired intensities. Thus, the exact diameter and location of the Island Apertures [9] may be optimized to obtain the desired intensity distribution incident on the target.

Island Blocks [5] and Island Apertures [9] can be used together when there is a wide range of intensity modulation, e.g. $0.01 \leq IRF \leq 0.99$, as is possibly the case for the central region of IMET beams and the edges of segmented ECT beams.

Preferably, the Intensity Reduction Factor (IRF) for bolus ECT should be between about 0.7 and 1.0 when using Island Blocks [5]. There are multiple solutions of (d, r) for equation 3 for Islands [5] of circular cross-section packed in a hexagonal grid that provide an IRF of between 0.70 and 1.00. As the values of (d,r) increases, the number of Islands needed decreases. However, if the values of (d, r) are too large, there will be insufficient scatter beneath the Island Blocks [5] to create the desired, reduced intensity distribution.

Example 1

As an example, FIG. 1 illustrates a collection of circular Island Blocks [5] of varying diameter located on a hexagonal grid (0.58 cm spacing) inside the aperture of a custom electron collimating insert. This is a prototype insert where an approximately square beam (field) is half-modulated. The diameters of the Island Blocks [5] comprising the intensity modulator vary from about 0.15 cm (IRF 0.94) in the right most region to about 0.4 cm (IRF 0.54) at the left. The Island Blocks [5] used in this example were made from tungsten and were 0.6 cm in length.

Example 2

The relative intensity profile for the prototype modulator described in example one was measured 2 cm deep in a water tank with the distance from the electron source to the water surface at 100 cm SSD. FIG. 6 illustrates the relative intensity profile (from left to right) through the center of the region containing Island Blocks [4] in FIG. 1.

Example 3

Figure 8:
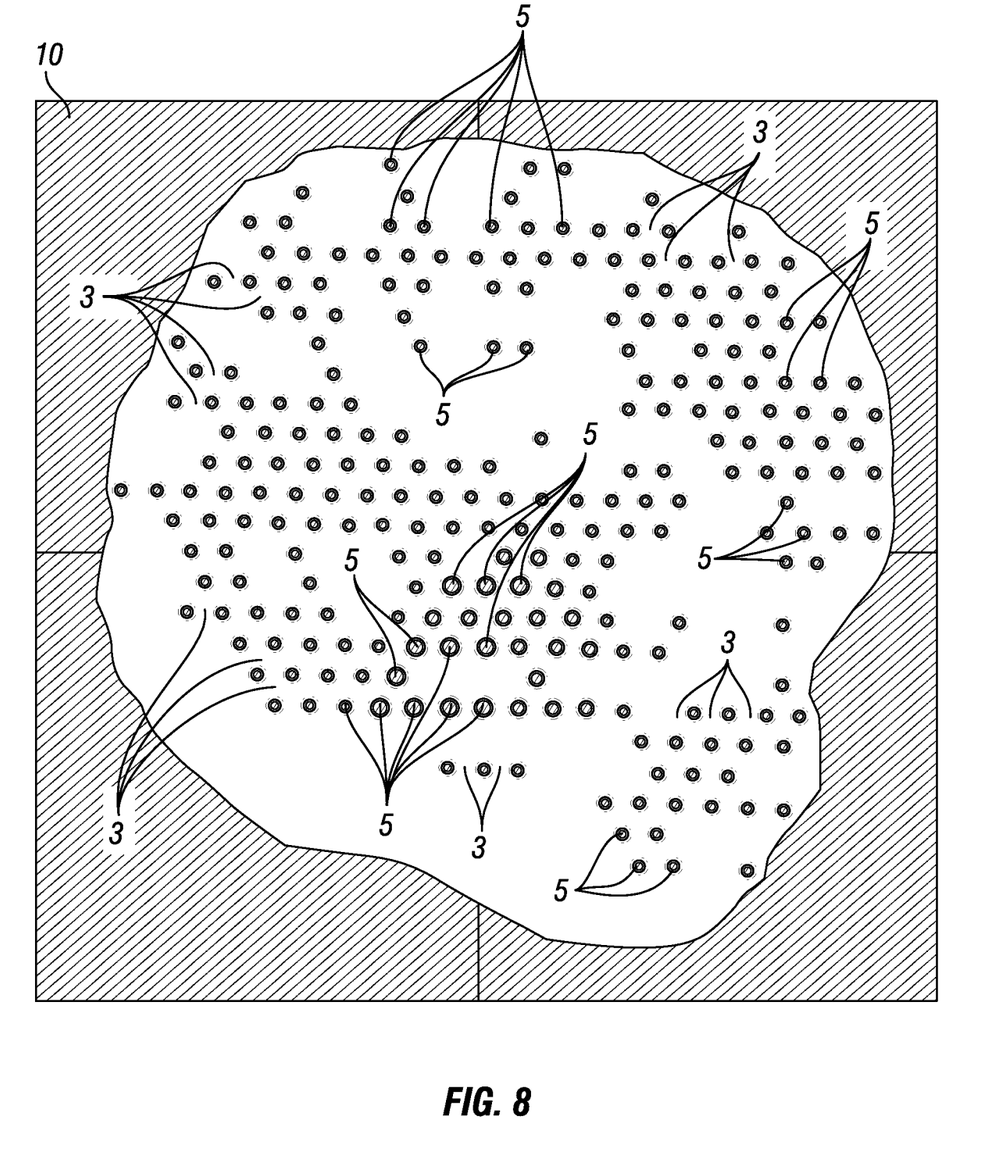
FIG. 8 displays a schematic of a beam's eye view of a patient intensity modulator, which includes Island Blocks of varying diameters located on a hexagonal grid and embedded in an electron-transparent substrate that fits within the collimating aperture of the collimating insert defining the electron beam.

FIG. 8 depicts a modulator designed from an actual patient treated with electron beam therapy. Here the diameter and placement of the Island Blocks [5] were designed to deliver a more uniform dose to the patient's PTV. The resulting intensity pattern incident on the patient is plotted using isointensity contours in FIG. 7.

The invention claimed is:

1. A method for passively modulating electron beam intensity spatially for an electron beam used in electron beam therapy comprising,
   a. generating the electron beam with an energy between 6 and 20 million electron volts;
   b. directing the electron beam through a beam defining aperture of an electron beam collimator and an intensity modulating insert, which is located near it and near a patient planning target volume; and
   impinging the electron beam, after it passes through the intensity modulating insert and the beam defining aperture of the electron beam collimator, onto the planning target volume of a patient,
Wherein the intensity modulating insert comprises a plurality of electron Island Blocks imbedded in an essentially electron transparent substrate, wherein the electron Island Blocks are sized and spaced so that parts of the electron beam are blocked, while the remainder of the electron beam passes through the electron transparent substrate without loss of significant energy thereby producing the modulated electron beam with a two-dimensional, non-homogenous spatial distribution of electron beam intensity, without significantly changing the energy of said electron beam, and is patient specific.

2. The method as in claim 1 wherein the electron Island Blocks may be columns of circular, square, rectangular, hexagonal, or other polygonal cross sections.

3. The method as in claim 1 wherein the electron Island Blocks are columns constructed of a dense metal of such thickness that it completely blocks electrons that impinge on said electron Island Blocks, wherein the dense metal is selected from the group consisting of tungsten, lead, copper, iron, and a heavy metal alloy.

4. The method as in claim 3 wherein the electron Island Blocks are constructed of tungsten.

5. The method as in claim 3 wherein the electron Island Blocks are constructed of a medically inert materials.

6. The method as in claim 1 wherein the electron Island Blocks have a cross-section with area equaling that of a circle between 0.05 cm and 1.0 cm in diameter.

7. The method as in claim 1 wherein the electron Island Blocks' centers fall on a hexagonal, rectangular, or other grid where grid locations are separated by distances between 0.1 cm and 5.0 cm.

8. A method for passively modulating electron beam intensity spatially for an electron beam used in electron beam therapy comprising,
   a. generating the electron beam with an energy between 6 and 20 million electron volts;
   directing the electron beam through a beam defining aperture of an electron beam collimator and an intensity modulating insert which is located near the electron beam collimator and near a patient panning target volume;
   impinging the electron beam, after it passes through the intensity modulating insert and the beam defining aperture of the electron beam collimator, onto the patient planning target volume,
Wherein the intensity modulating insert comprises a plurality of Island Apertures arrayed in an electron blocking substrate, wherein the Island Apertures are sized and spaced so that parts of the electron beam pass through the Island Apertures, while the remainder of the electron beam is totally blocked by the electron blocking substrate thereby modulating the electron beam energy without loss of significant energy thereby producing the modulated electron beam with a two-dimensional, non-homogenous spatial distribution of electron beam intensity, without significantly changing the energy of said electron beam, and is patient specific.

9. The method as in claim 8 wherein the Island Apertures may be circular, square, rectangular, hexagonal, or other polygonal cross sections.

10. The method as in claim 8 wherein the electron blocking substrate is constructed of a dense metal that completely blocks electrons that impinge on the electron blocking substrate, wherein the dense metal is selected from the group consisting of tungsten, lead, copper, iron, and a heavy metal alloy.

11. The method as in claim 10 wherein the electron blocking substrate is constructed of medically inert materials.

12. The method as in claim 8 wherein the Island Apertures have a cross-section with areas equaling that of a circle between 0.05 cm and 1.0 cm in diameter.

13. The method as in claim 8 wherein the Island Apertures' centers fall on a hexagonal, rectangular, or other grid where grid locations that are separated by distances between 0.1 cm and 5.0 cm.

14. A method for passively modulating electron beam intensity spatially for an electron beam used in electron beam therapy comprising,
   a. generating the electron beam with an energy between 6 and 20 million electron volts;
   b. directing the electron beam through a beam defining aperture of an electron beam collimator and an intensity modulating insert which is located near the electron beam collimator and near a patient planning target volume; and
   impinging the electron beam, after it passes through the intensity modulating insert and the beam defining aperture of the electron beam collimator, onto the patient planning target volume,
Wherein the intensity modulating insert comprises a plurality of electron Island Blocks imbedded in an essentially electron transparent substrate in combination with a plurality of Island Apertures arrayed in an electron blocking substrate, wherein the electron Island Blocks and the Island Apertures are sized and spaced so that parts of the electron beam are completely blocked, while the remainder of the electron beam passes through the intensity modulating insert without loss of significant energy thereby producing the modulated electron beam with a two-dimensional, non-homogenous spatial distribution of electron beam intensity, without significantly changing the energy of said electron beam, and is patient specific.

15. The method as in claim 14 wherein the electron Island Blocks and Island Apertures may be the same shape or different shapes selected from the group consisting of circular, square, rectangular, hexagonal, and other polygonal cross sections.

16. The method as in claim 14 wherein the electron Island Blocks and the electron blocking substrate are constructed of a dense metal that completely blocks electrons, wherein the dense metal is selected from the group consisting of tungsten, lead, copper, iron, and a heavy metal alloy, wherein the dense metal used for the electron Island Blocks may be the same as or different from the dense metal used for the electron blocking substrate.

17. The method as in claim 16 wherein the electron Island Blocks are constructed of tungsten and the electron blocking substrate is constructed of copper.

18. The method as in claim 16 wherein the electron Island Blocks and the electron blocking substrate are constructed of medically inert materials.

19. The method as in claim 14 wherein the electron Island Blocks and the Island Apertures have cross-sections with areas equaling that of circles between 0.05 cm and 1.0 cm in diameter.

20. The method as in claim 14 wherein the electron Island Blocks' centers fall on hexagonal, rectangular, or other grids where the grid locations are separated by between 0.1 cm and 5.0 cm and the Island Apertures' centers fall on hexagonal, rectangular, or other grids where grid locations are separated by between 0.1 cm and 5.0 cm.

21. The method as in claim 1 wherein the intensity modulating insert is located approximately 10 cm above the planning target volume of the patient.

22. The method as in claim 8 wherein the intensity modulating insert is located approximately 10 cm above the planning target volume of the patient.

23. The method as in claim 14 wherein the intensity modulating insert is located approximately 10 cm above the planning target volume of the patient.

\* \* \* \* \*